United States Patent [19]

Matsuura et al.

[11] 4,127,595
[45] Nov. 28, 1978

[54] PROCESS FOR PRODUCING BENZANTHRONE

[75] Inventors: Ryo Matsuura, Yamato; Shuichi Nakatani; Kazuya Nagaoka, both of Yokohama; Kouji Kusabe, Kawasaki; Mikio Kaseda, Yokohama, all of Japan

[73] Assignee: Kawasaki Kasei Chemicals Ltd., Tokyo, Japan

[21] Appl. No.: 845,379

[22] Filed: Oct. 25, 1977

[30] Foreign Application Priority Data

Nov. 17, 1976 [JP] Japan .................................. 51-137974

[51] Int. Cl.$^2$ .......................... C07C 49/70; C09B 3/02
[52] U.S. Cl. .................................................... 260/352
[58] Field of Search ............................... 260/352, 369

[56] References Cited

U.S. PATENT DOCUMENTS

| 1,929,866 | 10/1933 | Fairweather et al. | 260/369 |
| 2,495,229 | 1/1950 | Dawsey et al. | 260/369 |

FOREIGN PATENT DOCUMENTS

| 482,839 | 9/1929 | Fed. Rep. of Germany | 260/352 |
| 720,467 | 4/1942 | Fed. Rep. of Germany | 12/10 |
| 28,593 | 10/1905 | United Kingdom | 260/352 |

Primary Examiner—Allen B. Curtis
Assistant Examiner—Raymond Covington
Attorney, Agent, or Firm—Oblon, Fisher, Spivak, McClelland & Maier

[57] ABSTRACT

Benzanthrone is produced by reacting a hydroanthraquinone having 1,4-dihydro ring with acrolein or an acrolein precursor in the presence of a dehydration catalyst.

10 Claims, No Drawings

PROCESS FOR PRODUCING BENZANTHRONE

BACKGROUND OF THE INVENTION

1. Field of the Invention

The present invention relates to a novel process for producing benzanthrone, more particularly, it relates to a novel process for producing benzanthrone by reacting a specific hydroanthraquinone with acrolein.

2. Description of the Prior Art

Benzanthrone is an important compound as the starting material for producing Indanthrene dyes and pigments.

It has been known to produce benzanthrone by the following processes. (1) Anthraquinone is dissolved into sulfuric acid and a mixture of metallic powder and glycerin is added to the solution to reduce anthraquinone and simultaneously, the reaction product is further reacted with the compound resulted by dehydration of glycerin in an addition-reaction (B10S 987 and F1AT 1313). (2) Benzanthrone is produced by reacting an anthrahydroquinone ester such as acetate and sulfate which is obtained by reducing and esterifying anthraquinone, with acrolein in the presence of a dehydration catalyst such as sulfuric acid and piperidine in a solvent of acetic acid. (DRP 720,467). (3) Benzanthrone is produced by condensing α-benzoylnaphthalene at higher than 150° C. in the presence of aluminum chloride catalyst or at 120° C. in the presence of iron chloride catalyst. (DRP 239,761).

However, in the process (2), the expensive metallic powder is used to reduce anthraquinone and anthraquinone is esterified with acetic anhydride etc. whereby the complicated steps are needed, and the reaction velocity in the production of benzanthrone is slow and the cost is expensive and the separation of the metal ions is not easy in the waste treating step.

In the process (3), the yield is too low such as 75% and many reaction steps are needed and large amounts of the by-products are produced. Accordingly, it is not an industrial process.

In the process (1), which is mainly employed as an industrial process, 7 to 10 times of sulfuric acid to anthraquinone should be used as the solvent for anthraquinone. Accordingly, when benzanthrone is precipitated by diluting the reaction product with water, a large amount of dilute sulfuric acid waste having high COD load may be discharged. The precipitated crystals are fine whereby the filtration is inferior. The compounds produced by reducing anthraquinone are unstable in sulfuric acid at the elevated temperature and the control of temperature in the addition-cyclization reaction is not easy and sometimes, the bubbling is caused whereby the control of the addition-cyclization reaction is not easy. Moreover, the metal powder having uniform particle size distribution should be used as the reducing agent whereby it is expensive. There is high possibility of the accident of explosion on hydrogen gas generated by using the reducing agent. The separation of metal ions discharged in the waste water is not easy. These disadvantages have been found.

The inventors have studied to overcome the disadvantages found in the conventional processes.

SUMMARY OF THE INVENTION

It is an object of the present invention to provide a process for producing benzanthrone in economical and stable conditions without a trouble of a pollution, complicated steps, an expensive raw material etc.

The foregoing and other objects of the present invention have been attained by producing benzanthrone by reacting a hydroanthraquinone having 1,4-dihydro ring with acrolein or an acrolein precursor in the presence of a dehydration catalyst.

DETAILED DESCRIPTION OF THE PREFERRED EMBODIMENTS

The present invention is to provide a process for producing benzanthrone reacting 1 a hydroanthraquinone having 1,4-dihydro ring (which is produced by the Diels-Alder reaction of benzoquinone or naphthoquinone with butadiene or deriving from the reaction product) with 2 acrolein or an acrolein precursor in the presence of a dehydration catalyst, without the serious disadvantages in the conventional processes such as the discharge of large amount of sulfuric acid waste and the use of large amount of metal powder, whereby the advantageous process from the viewpoints of the prevent of pollution and the economical operation is attained.

The process of the present invention will be further illustrated.

Hydroanthraquinones used in the present invention include 1,4,4a,9a-tetrahydroanthraquinone, (hereinafter referring to as 1,4,4a,9a-THAQ), 1,4-dihydroanthrahydroquinone (hereinafter referring to as 1,4-DHAHQ), 1,4-dihydroanthraquinone (hereinafter referring to as 1,4-DHAQ), a mixture thereof; and quinhydrones thereof such as quinhydrone of 1,4-DHAQ and 1,4-DHAH Q, quinhydrone of 1,4-DHAQ and anthrahydroquinone; and hydroanthraquinones obtained by reducing anthraquinone and by the Diels-Alder reaction of 1 mole of benzoquinone with 2 moles of butadiene.

It is usually preferable to use 1,4,4a,9a-THAQ, 1,4-DHAHQ, 1,4-DHAQ, a mixture thereof or a quinhydrone thereof from the viewpoint of a commercial availability. When 1,4-DHAQ is used, the reaction velocity is relatively slow. However, when 1,4-DHAQ is mixed with 1,4-DHAHQ and/or 1,4,4a,9a-THAQ, the reaction velocity is remarkably promoted.

Hydroanthraquinones can be easily produced by Diels-Alder reaction of a quinone such as benzoquinone and naphthoquinone with butadiene. For example, 1,4,4a,9a-THAQ is produced by reacting 1,4-naphthoquinone with butadiene in an organic solvent such as benzene, xylene etc. 1,4-DHAHQ is produced by an enolization of 1,4,4a,9a-THAQ in an organic solvent in the presence of a mineral acid as the catalyst. 1,4-DHAQ is produced by an oxidation of 1,4,4a,9a-THAQ with molecular oxygen in an aqueous medium at pH of 7 to 12.

In the process of the present invention, acrolein can be supplied as acrolein itself or an acrolein precursor which is converted to acrolein in the reaction such as glycerin, chlorohydrin, β-hydroxypropionaldehyde, acrolein acetal, a mixture of formaldehyde and acetaldehyde etc.

The amount of acrolein is usually less than 4 moles preferably less than 2 moles especially about 1.2 moles per 1 mole of hydroanthraquinone.

In the present invention, the reaction of a hydroanthraquinone with acrolein can be performed by heating them in the presence of a dehydration catalyst.

Suitable dehydration catalysts include inorganic acidic compounds such as sulfuric acid, hydrochloric acid, hydrogen chloride, acidic sulfate, polyphosphoric acid, phosphoric acid, perchloric acid, phosphorus pentoxide; non-metal chlorides such as phosphorus oxychloride, phosphorus chloride; metal chlorides such as zinc chloride, copper chloride, ferric chloride, aluminum chloride; organic acids such as paratoluenesulfonic acid, xylenesulfonic acid, naphthalenesulfonic acid, trichloroacetic acid, trifluoroacetic acid, trifluoromethanesulfonic acid; and partial ester of polyphosphoric acid; ion exchange resin (acid type) etc.

The amount of the dehydration catalyst is enough to be less than the same weight of the hydroanthraquinone, and it is selected depending upon a kind of the hydroanthraquinone and a kind and amount of the solvent, and it is usually in a range of about 1 to 30 wt. %.

In the process of the present invention, it is preferable to use a solvent in order to prevent a side reaction and to perform smoothly the reaction. An organic solvent is usually used.

Suitable solvent include aromatic hydrocarbons such as benzene, toluene, xylene, naphthalene and tetraline, decaline; halogenated hydrocarbons such as trichlorobenzene, trichloroethane and trichloroethylene; alcohols such as glycerine (which is also used as the acrolein precursor), butanol, amyl alcohol and heptanol; monoethers or diethers of ethyleneglycol or polyethyleneglycol; cellosolves, such as ethylcellosolve; ethers such as diphenyl ether and dioxane; sulfoxides such as sulfolane; lower aliphatic acids such as formic acid, acetic acid, propionic acid and butyric acid; esters such as ethyl acetate, propyl acetate, butyl acetate etc. It is preferable to use the solvent which is substantially stable in the reaction and it is especially preferable to use a lower aliphatic acid such as acetic acid, propionic acid. A mixture of the solvent can be used. Even though the solvent contains a small amount of water, there may be no trouble in the reaction.

The amount of the solvent is enough to dissolve or disperse the hydroanthraquinone, and it is usually in a range of about 1 to 20 times (by weight) of the hydroanthraquinone. Excess of the solvent can be used without adversely affecting to the reaction though it is not economical.

The reaction temperature is selected depending upon kinds of the starting material, the dehydration catalyst and the solvent, and it is usually lower than 250° C. When acrolein is used, the reaction temperature is preferably lower than 150° C. especially in a range of 50° to 130° C.

When the reaction temperature is too high, a polymerization of acrolein etc. is caused to increase the by-products. On the other hand, when the reaction temperature is lower than 50° C., the reaction velocity is lowered and the selectivity is also lowered.

When glycerin is used as the acrolein precursor, the reaction temperature is preferably in a range of about 140° to 250° C.

The reaction pressure is preferably the atmospheric pressure and can be lower or higher pressure.

The reaction time is depending upon the temperature etc., and it is usually longer than 0.5 hour and shorter than 6 hours.

In the process of the present invention, a mixture of the hydroanthraquinone, the solvent and acrolein or the acrolein precursor is prepared and then the dehydration catalyst such as sulfuric acid is added to react them at suitable temperature or the mixture is reacted for suitable time without an addition of the dehydration catalyst and then, the reaction is continued after an addition of the dehydration catalyst. When the dehydration catalyst is sulfuric acid etc., it is preferably diluted with the solvent before the addition whereby the severe side reaction of acrolein can be prevented.

It is also possible to feed acrolein or the acrolein precursor to a mixture of the hydroanthraquinone and suitable amounts of the dehydration catalyst in batch or continuous system.

When a mixture of 1,4-DHAQ and 1,4,4a,9a-THAQ and/or 1,4-DHAHQ is used, it is preferable to add a mixture of acrolein or the acrolein precursor and 1,4,4a,9a-THAQ and/or 1,4-DHAHQ to a solution or a suspension of 1,4-DHAQ and the dehydration catalyst.

In accordance with this process, most of benzanthrone is crystallized by cooling the reaction mixture as benzanthrone crystals which have excellant filtration property whereby the separation of benzanthrone is easy.

The reaction mechanism of the process of the present invention has not clearly found. It has been considered that a benzanthrone precursor of dihydrobenzanthrone is formed at the completion of the reaction when the tetrahydroanthraquinone such as 1,4,4a,9a-THAQ or 1,4-DHAHQ is used as the starting material of hydroanthraquinone. However, the dihydrobenzanthrone is easily oxidized and the dihydrobenzanthrone is not isolated and benzanthrone is obtained.

The object compound can be separated from the reaction mixture by the conventional processes, for example, the solvent is separated and recovered by a distrillation under a reduced pressure or the atmospheric pressure after a neutralization of the dehydration catalyst in the reaction mixture if necessary, or the reaction mixture is cooled and the precipitated crystals are filtered or the reaction mixture is diluted with water and the precipitated crystals are filtered.

In the neutralization, a base such as oxides, hydroxides or weak acid salts e.g., carbonates and acetates of alkali metals or alkaline earth metals; ammonia, ammonia water, and ammonium salts e.g., ammonium carbonate and ammonium acetate is used.

When it is necessary to purity the resulting crystals of benzanthrone, the purification can be attained by a sublimation, a distillation, a recrystallization from a solvent solution, and a purification by adsorption and elution with a column filled with alumina etc.

The effects of the present invention are as follows. (1) It is unnecessary to use a metal powder for the reduction of anthraquinone in sulfuric acid and to employ the dangerous reduction generating hydrogen gas as that of the conventional process, when hydroanthraquinones are used. (2) It is unnecessary to use a large amount of sulfuric acid as that of the conventional process, whereby the waste solution-treating step can be simplified and most of the solvent can be recovered to reuse it. (3) It is possible to obtain crystals of benzanthrone having high purity because the amount of the polymerized by-products produced in the reaction are small.

The present invention will be illustrated by certain examples in detail. In the examples, the terms of "part" and "%" mean "part by weight" and "% by weight".

EXAMPLE 1

In a reactor equipped with a stirrer, a reflux condenser, 32.9 wt. parts of 1,4,4a,9a-THAQ, 600 wt. parts of acetic acid and 11.6 wt. parts (1.2 molar ratio to THAQ) of 90% acrolein were charged, and the mixture was heated at the boiling point under stirring to react them for 30 minutes, and then, 2.0 wt. parts of 95% sulfuric acid was added to the reaction mixture to react them for 3 hours. After the reaction, the reaction mixture was poured into 6000 wt. parts of water under stirring whereby yellowish white emulsion was resulted. The emulsion was stirred for 1 hour in air whereby the aggregation of crystals was performed to form the yellow floc of crystals. The crystals were filtered and washed with water and dried at 70° C. under a reduced pressure, whereby 33.0 wt. parts of the product was obtained.

The product was analyzed by a high speed liquid chromatography to find 89% of a content of benzanthrone, 82 mole % of a yield and 157° to 160° C. of a melting point.

The product was recrystallized from chloroform to obtain yellow acicular crystals having a melting point of 172° to 173° C.

The infrared spectrums of the crude product and the recrystallized product were respectively conformed to that of benzanthrone.

EXAMPLE 2

In accordance with the process of Example 1, 21.2 wt. parts of 1,4-DHAHQ, 200 wt. parts of acetic acid, 7.47 wt. parts (1.33 molar ratio to DHAHQ) of 90% acrolein and 2.1 wt. parts of 95% sulfuric acid are charged in the reactor and the mixture was heated at 90° C. under stirring to react them for 1 hour. After the reaction, 3.4 wt. parts of sodium acetate was added to neutralize sulfuric acid, and then 150 wt. parts of acetic acid was recovered by a distillation.

The residue was poured into 500 wt. parts of water and it was throughly stirred in air to form yellow floc of crystals. The crystals were filtered and dried at 70° C. under a reduced pressure to obtain 22.4 wt. parts of yellow crystals as the product.

The product was analyzed by a high speed liquid chromatography to find 87% of a content of benzanthrone and 85 mole % of a yield.

EXAMPLE 3

In accordance with the process of Example 1, 1.0 wt. part of 1,4-DHAQ, 10.0 wt. parts of acetic acid, 0.4 wt. part of 90% acrolein (1.35 molar ratio to DHAQ) and 0.01 wt. part of 95% sulfuric acid were charged in a reactor and the mixture was heated at the boiling point under stirring to react them for 4 hours. After the reaction, 8.0 wt. parts of acetic acid was distilled off under a reduced pressure. The residue was cooled and the precipitated yellow crystals were filtered and washed with water and dried to obtain 1.0 wt. part of the yellow product.

The product was analyzed by a high speed liquid chromatography to find 50% of a content of benzanthrone and 46 mole % of a yield. The other components in the reaction mixture were mainly the unreacted 1,4-DHAQ and a small amount of anthraquinone.

EXAMPLE 4

In accordance with the process of Example 1, 30.0 wt. parts of quinhydrone of 1,4-DHAQ and 1,4-DHAHQ, 9.5 wt. parts of 90% acrolein (1.07 molar ratio to DHAHQ), 200 wt. parts of acetic acid and 2.0 wt. parts of sulfuric acid were used to obtain 31.0 wt. parts of yellow crystals of the product. The product was analyzed by the method of Example 1 to find 89% of a content of benzanthrone and 84 mole % of a yield.

EXAMPLE 5

In accordance with the process of Example 1, 10 wt. parts of 1,4-DHAHQ, 3.4 wt. parts of 90% acrolein (1.16 molar ratio to DHAHQ), 200 wt. parts of acetic acid and a dehydration catalyst of 1 wt. part of paratoluenesulfonic acid, 1 wt. part of ferric chloride, 5 wt. parts of 36% hydrochloric acid or 20 wt. parts of polyphosphoric acid were used to obtain the following results.

Table

| Dehydration catalyst | Amount of product (wt. parts) | Content of benzanthrone in product (%) | Yield of benzanthrone (mole %) |
|---|---|---|---|
| Paratoluene-sulfonic acid | 11.1 | 67 | 69 |
| Ferric chloride | 10.4 | 76 | 73 |
| 36% hydrochloric acid | 11.5 | 66 | 70 |
| Polyphosphoric acid | 11.2 | 57 | 59 |

EXAMPLE 6

In accordance with the process of Example 1, 1 g of 1,4-DHAHQ, 20 ml of toluene and 0.4 ml of 90% acrolein (0.336 g:1.14 molar ratio to DHAHQ) were charged in the reactor and the mixture was stirred at the boiling point to react them for 30 minutes, and then 0.1 g of paratoluenesulfonic acid was added to the mixture to react them for 3 hours. After the reaction, 0.1 g of sodium acetate was added to the reaction mixture to neutralize paratoluenesulfonic acid, and then, toluene was distilled and recovered under a reduced pressure. The residue was washed with about 10 times of water and filtered and washed water to obtain 1.49 g of the product. The product was analyzed to find 45% of a content of benzanthrone and 62 mole % of a yield.

When xylene was used instead of toluene, the same results were obtained.

EXAMPLE 7

In accordance with the process of Example 1, 5.0 wt. parts of quinhydrone of 1,4-DHAHQ and 1,4-DHAQ, 0.8 wt. part of conc. sulfuric acid and 100 wt. parts of propionic acid were charged in a reactor and then, 1.77 wt. parts of acrolein was added to react them at 130° C. for 1.5 hours.

After the reaction, the reaction mixture was poured into 10 times of water and the precipitated crystals were filtered and washed with water and dried to obtain 5.86 wt. parts of the product.

The product was analyzed by the high speed liquid chromatography to find 71% of a content of benzanthrone and 76 mole % of a yield.

EXAMPLE 8

In accordance with the process of Example 1, 5 wt. parts of 1,4,4a,9a-THAQ, 50 wt. parts of glycerin, and 0.98 wt. part of paratoluenesulfonic acid were charged in the reactor to react them at 150° C. for 2 hours. After the reaction, the reaction mixture was poured into 10 times of water and the precipitated crystals were filtered and washed with water and dried the crystals to obtain 5.56 wt. parts of dark green crystals of the product.

The product was analyzed by the high speed liquid chromatography to find 40.4% of a content of benzanthrone and 41.4 mole % of a yield. The product contained the main component of benzanthrone as well as 1,4-DHAQ.

EXAMPLE 9

In a reactor equipped with a stirrer, a reflux condenser and a dropping funnel, 25 wt. parts of acetic acid, 3.23 wt. parts of 1,4-DHAQ and 0.8 wt. part of paratoluenesulfonic acid were charged and the mixture was heated at 110° C. under stirring to disperse 1,4-DHAQ, and then, a mixture of 1.17 wt. parts of 1,4,4a,-9a-THAQ, 1.9 wt. parts of acrolein and 25 wt. parts of acetic acid was added dropwise to the dispersion through the dropping funnel during 95 minutes. After the addition, the mixture was heated to react them for 60 minutes.

After the reaction, the reactor was cooled and the precipitated crystals were filtered and washed with methanol and dried to obtain 3.63 wt. parts of the crystals as the primary crystals.

The crystals were analyzed by the high speed liquid chromatography to find 94.9% of a content of benzanthrone, 1.9% of anthraquinone, and less than 0.1% of dihydroanthraquinone.

The methanol washing solution and the filterate separated from the primary crystals were poured into 20 times of water and the precipitated crystals were filtered and washed with water and dried to obtain 1.62 wt. parts of crystals as the secondary crystals. The secondary crystals were analyzed to find 28% of a content of benzanthrone. Total yield of benzanthrone was 81 mole%.

EXAMPLE 10

In accordance with the process of Example 1, 1.0 wt. part of 1,4,4a,9a-THAQ, 20.0 wt. parts of acetic acid, 1.0 part of acrolein acetal (1.63 molar ratio to THAQ) and 0.1 wt. part of sulfuric acid were used to obtain 1.1 wt. parts of yellow crystals of the product. The product was analyzed by the method of Example 1 to find 61.3% of a content of benzanthrone and 62 mole % of a yield.

What is claimed is:

1. A process for producing benzanthrone which comprises reacting a hydroanthraquinone having 1,4-dihydro ring with acrolein or an acrolein precursor in the presence of a dehydration catalyst.
2. A process according to claim 1 wherein the hydroanthraquinone is the product produced by the Diels-Alder reaction of benzoquine or naphthoquinone with butadiene or a derivative thereof.
3. A process according to claim 1 wherein the hydroanthraquinone is 1,4,4a,9a-tetrahydroanthraquinone, 1,4-dihydroanthrahydroquinone, 1,4-dihydroanthraquinone or a mixture thereof.
4. A process according to claim 1 wherein the reaction is carried out in the presence of a solvent.
5. A process according to claim 4 wherein the solvent is an organic solvent.
6. A process according to claim 5 wherein the organic solvent is a lower aliphatic acid.
7. A process according to claim 6 wherein the lower aliphatic acid is acetic acid or propionic acid.
8. A process according to claim 1 wherein the dehydration catalyst is an acidic compound.
9. A process according to claim 8 wherein the acidic compound is an inorganic acidic compound, metal chloride or an organic acid.
10. A process according to claim 1 wherein the reaction is carried out at 50° to 250° C.

* * * * *